(12) United States Patent
Vries et al.

(10) Patent No.: US 6,235,927 B1
(45) Date of Patent: May 22, 2001

(54) PROCESS FOR THE SEPARATION OF A MIXTURE OF ENANTIOMERS

(75) Inventors: Ton R. Vries, Groningen; Hans Wijnberg, Haren; Erik Van Echten, Assen; Lumbertus A. Hulshof, Baarlo; Quirinus B. Broxterman, Sittard, all of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 08/955,612

(22) Filed: Oct. 22, 1997

(30) Foreign Application Priority Data

Oct. 23, 1996 (NL) .................................................. 1004346

(51) Int. Cl.$^7$ .................................................. C07B 55/00
(52) U.S. Cl. ............................ 562/401; 560/38; 564/303; 564/304; 558/354; 558/73; 544/330; 544/98; 546/184
(58) Field of Search ............................... 562/401; 560/38; 564/303, 304; 558/354, 73; 544/336, 98; 546/184

(56) References Cited

U.S. PATENT DOCUMENTS 4,642,205 * 2/1987 Acs et al. ............................. 562/401

* cited by examiner

*Primary Examiner*—Samuel Barts
(74) *Attorney, Agent, or Firm*—Pillsbury Winthrop LLP

(57) ABSTRACT

A diastereomer complex obtained via a process for the separation of enantiomers is disclosed, wherein separation can be rapidly effected such that enantiomers are obtained with high e.e. values. The process pets the separation of mixtures of enantiomers in which more than one resolving agent is used, of which at least one resolving agent is optically active, and which yields a diastereomer complex containing at least two resolving agents in optically active form. The process provides for, inter alia, a diastereomer complex having at least three compounds of which at least two compounds are resolving agents in optically active form, and at least one compound is an onantiomer in optically active form. Also provided is a diastereomer complex having at least three compounds of which at lea one compound is a resolving agent in optically active form, and at least two compounds which are enantiomers in optically active form.

15 Claims, No Drawings

PROCESS FOR THE SEPARATION OF A MIXTURE OF ENANTIOMERS

FIELD OF THE INVENTION

The invention relates to a process for the separation of a mixture of enantiomers.

BACKGROUND INFORMATION

Mixtures of enantiomers are obtained, for instance, in reactions that do not, or only to a small extent, proceed stereoselectively and in reactions in which there is no complete inversion or retention. The physical properties of enantiomers, such as boiling point, melting point and the like, are the same, so that a mixture of enantiomers cannot be separated using the customary separation techniques. In one of the methods for the separation of mixtures of enantiomers, for instance racemic mixtures, an optically active resolving agent is used to convert both enantiomers into the corresponding diastereomers. As the physical properties of these diastereomers do differ, the diastereomers can, at any rate in principle, subsequently be separated by, for instance, crystallization or chromatography, both diastereomers being obtained in substantially chemically pure and optically enriched form. The diastereomer can in a third step again be separated into the corresponding, optically enriched enantiomer and the optically active resolving agent. Several processes and optically active resolving agents for the separation of enantiomers are, for instance, extensively described in "Stereochemistry of Organic Compounds" by E. L. Eliel and S. H. Wilen (Wiley Interscience, 1994).

However, it is common knowledge that finding the right resolving agent for the separation of mixtures of enantiomers by crystallization of a mixture of diastereomers is in practice a laborious and highly time-consuming process, for a correct choice of the resolving agent cannot in advance be made, not even when applying advanced techniques such as, for instance, computer simulations or X-ray diffraction, and thus has to be found by trial and error for each mixture of enantiomers anew. This implies that for the separation of enantiomers via diastereomers often many experiments have to be conducted, while the individual experiments may take a long time on account of tedious crystallization. Moreover, in not nearly all the cases is a suitable resolving agent found. It will therefore be clear that the search for a good resolving agent for the separation of mixtures of enantiomers of a compound and the conditions under which good results are obtained is a time-consuming matter and the chance of success is unpredictable.

SUMMARY AND OBJECTS OF THE INVENTION

The subject invention therefore aims to provide a process by which a separation of enantiomers can be effected rapidly and with a high chance of success and by which the desired enantiomer is obtained with a high e.e.

According to the invention this is among other things achieved by means of a process for the separation of mixtures of enantiomers in which more than one resolving agent is used, of which at least one resolving agent is optically active, and which yields a diastereomer complex that contains at least two resolving agents in optically active form. It has been found that with the process according to the invention more often than in resolutions with a single resolving agent, directly a crystalline product is obtained instead of an oil, so that immediately the result of the experiment is known. Subsequent experiments can consequently be done in a shorter period of time. Moreover, the process according to the invention allows testing of several resolving agents and/or mixtures of enantiomers in one single experiment, so that the process according to the invention also allows rapid selection of suitable resolving agents. In addition, it has been found that in many cases the enantiomeric excess (e.e.) of the desired resolved enantiomer is higher when more than one resolving agent is used than when use is made of a single resolving agent. Furthermore it has been found that mixtures of enantiomers, which themselves cannot be resolved using a certain resolving agent, could be resolved when they were applied in combination with mixtures of enantiomers of similar structure.

According to the invention it is also possible to separate a mixture of enantiomer mixtures, that is, a mixture of two or more different chemical compounds in which both enantiomers of each compound occur, into substantially optically active enantiomers using one or more resolving agents, of which at least one resolving agent is optically active. This is elucidated with reference to the following example, in which only one resolving agent is used: A mixture of the enantiomers of, for instance, compounds A, B and C (the mixture therefore contains 3 mixtures of enantiomers: 3 pairs of two enantiomers each) is separated into a mixture containing optically enriched enantiomers of compounds A, B and C, use being made of only a single optically active resolving agent. Of this second mixture subsequently the components A, B and C are separated from the resolving agent. After this, the components A, B and C are separated by means of the customary separation techniques. Of course, it is also possible to use a combination of different resolving agents. This way, in a single experiment many combinations can be rapidly tested.

The invention relates among other things to a diastereomer complex, for instance a salt, comprising at least three compounds of which at least one compound is a resolving agent in optically active form and at least one compound is an enantiomer in optically active form.

DETAILED DESCRIPTION OF THE INVENTION

A diastereomer complex of one or more optically active resolving agents and one or more enantiomers is understood to mean complexes in which the resolving agent(s) and the enantiomer(s) are bonded via one or more non-covalent bonds, for instance van der Waals interactions, II—II-interactions, inclusion, ionogenic bonds, coordination bonds, hydrogen bonds and/or a combination of such bonds.

As resolving agent use can be made of any compound that is suitable for converting a mixture of enantiomers via precipitation into a diastereomeric salt containing a mixture of enantiomers with a higher enantiomeric excess. The resolving agent may contain a metal, optionally with the associated ligands. Preferably, as optically active resolving agent use is made of a resolving agent with the highest possible e.e., for instance an e.e. >95%, in particular >98%, more in particular >99%.

The term enantiomer in this context refers to the mixture of enantiomers to be enriched. As mixture of enantiomers in principle all chiral compounds, in practice usually compounds containing at least one asymmetrical carbon atom, can be used. The enantiomers can for instance be compounds that contain at least an acid group, an amino group, a hydroxy group and/or a thiol group.

In principle a chemical compound that can be appropriately used as a mixture of enantiomers to be separated with an appropriate resolving agent, also represents an appropriate resolvent agent to be used in the separation of a mixture of enantiomers.

In the framework of this invention the term mixture of enantiomers means a mixture of the enantiomers of an optically active compound in any ratio.

Naturally, in the framework of this invention the same holds with respect to the separation of a mixture of enantiomers which already has a certain enantiomeric excess as for racemic mixtures.

In a particularly suitable embodiment the mixtures of enantiomers are separated via salt formation. Examples of mixtures of enantiomers that can suitably be separated via salt formation are acids, and bases in particular carboxylic acids, phosphoric acids, sulphonic acids, phosphinic acids, sulphinic acids, amines, acidic alcohols, amino acids, amino alcohols and acidic thiols.

Other examples of ways in which mixtures of enantiomers can suitably be separated according to the invention are separations via inclusion compounds, for which in principle any chiral compound forming an inclusion compound can be used, or separation via metal complexes, for instance as described in J. A. Gladysz & B. J. Boone, *Angew. Chem. Int. Ed. Engl.* 36, p. 576–577, 1997.

As an example of a possible use of the process according to the invention, the invention will now be elucidated with reference to the separation of a racemic mixture of an amine using at least two optically active acids or using at least one optically active acid and a non-optically active acid. A first commercially interesting use of the process according to the invention is the screening of resolving agents. In practice this is usually done at lab scale, with various acids, for instance 2–20, in particular 2–12, more in particular 2–6, simultaneously being used as resolving agents. The combination of acids found in the complex precipitated usually offers the best prospects of a good result, it probably being possible in a number of cases to leave out acids that are found in the complex in small amounts. Of course it is also possible that only one resolving agent, in this specific case one acid, is found in the complex. In that case the resolving agent preferably used will contain only one component.

The acids that upon screening at lab scale are selected may subsequently be used as agent in the form of a mixture of at least two, for instance 2–6, in particular 2–3 acids in the separation of a racemic mixture of the amine on an industrial scale. An optically active amine and a mixture of at least 2 acids are obtained from the resulting diastereomer mixture of salts.

Preferably, the resolving agents are of the same type, for instance resolving agents within a certain group. Examples of groups of resolving agents that can suitably be used in the process according to the invention are:

Substituted phosphoric acids, for example phosphoric acids of formula S1:

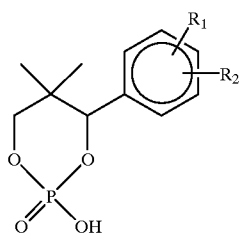

(S1)

where $R_1$ and $R_2$ each independently represent H, an alkyl group or an aryl group;

Optically active substituted tartaric acids, for instance tartaric acids of formula S2:

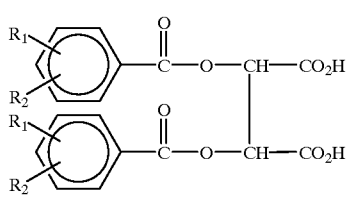

(S2)

where $R_1$ and $R_2$ are as defined above;

Substituted α-hydroxycarboxylic acids, for instance mandelic acids of formula S3;

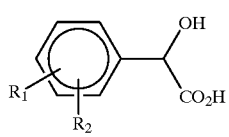

(S3)

where $R_1$ and $R_2$ are as defined above;

N-acylamino acids, substituted or not, for instance N-acylamino acids of formula S4:

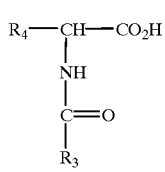

(S4)

where $R_3$ has a fixed meaning within a group, chosen from an alkyl group or an aryl group, and $R_4$ represents an aryl group, for instance an $R_1$ and $R_2$ substituted phenyl group with $R_1$ and $R_2$ as defined above, or an alkyl group, for instance an amino acid radical as occurring in natural amino acids, or where $R_4$ has a fixed meaning within a group, chosen from an aryl group, for instance an $R_1$ and $R_2$ substituted phenyl group with $R_1$ and $R_2$ as defined above, or an alkyl group, for instance an amino acid radical of natural amino acids, and $R_3$ represents an alkyl group or an aryl group.

A special example is acylated protein hydrolysate.
or of formula S5 (N-benzyloxycarbonyl amino acids):

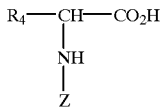
(S5)

where $R_4$ is as defined above;
N-carbamoyl amino acids, substituted or not, for instance N-carbamoyl amino acids of formula S6:

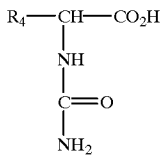
(S6)

where $R_4$ is as defined above. A special example is carbamoylated protein hydrolysate;
Substituted phenalkylamines, for instance phenalkylamines of formula S7:

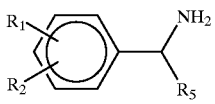
(S7)

where $R_1$ and $R_2$ may vary within a group as defined above and $R_5$ has a fixed meaning, chosen from alkyl, or $R_1$ and $R_2$ are fixed choices from the groups as defined above and $R_5$ varies within the alkyl group;
Amino acid amides, substituted or not, for instance amino acid amides of formula S8:

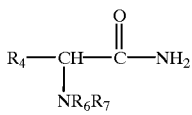
(S8)

where $R_4$ is as defined above, and $R_6$ and $R_7$ are chosen independently of each other from H and alkyl;
Substituted N-glucosamines, for instance N-glucosamines of formula S9:

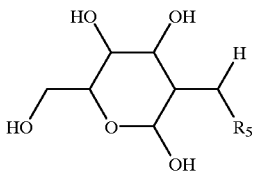
(S9)

where $R_5$ is as defined above;
Aryloxypropionic acids, for instance aryloxypropionic acids of formula S10:

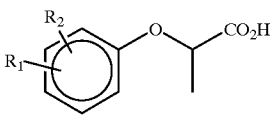
(S10)

where $R_1$ and $R_2$ are as defined above;
Optically active ethers of tartaric acids, for instance ethers of formula S11:

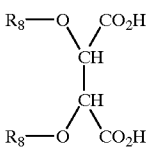
(S11)

where $R_8$ is preferably methyl or benzyl; optically active acetals of tartaric acids, for instance acetals of formula S12:

(S12)

where $R_3$ is as defined above and $R_3'$ independently represents the same groups and is not equal to $R_3$;
optically active alkanoylesters of tartaric acids, for instance of formula S13:

(S13)

where $R_5$ is as defined above;
phenylaminopropane diols, for instance of formula S14:

(S14)

where $R_1$ and $R_2$ are as defined above.
The substituents $R_i$ with i=1–8 preferably contain 1–30, particularly 1–20 C-atoms and may optionally be substituted with an alkyl group, alkoxy group, carboxyl group, alkoxycarbonyl group, amino group, nitro group, thio group, thioalkyl group, nitrile group, hydroxy group, acyl group or halogen.
Examples of suitable mixtures of enantiomers are:
α-amino acids and their derivatives with as formula (E1):

(E1)

where:
R$_4$ is as defined above
R$_6$ and R$_7$ are as defined above
R$_9$ stands for OH, alkoxy, NH$_2$
R$_{10}$ stands for H, alkyl and aryl and R$_4$ is not the same as R$_{10}$ α-aminonitriles, for instance of formula (E2):

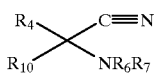
(E2)

where R$_4$, R$_6$, R$_7$ and R$_{10}$ are as defined above;
β-amino acids (and derivatives) for instance of formula (E3)

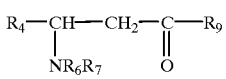
(E3)

where R$_4$, R$_6$, R$_7$ and R$_9$ are as defined above.
phenalkylamines, for instance of formula E4:

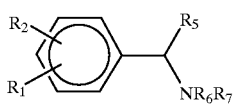
(E4)

where R$_1$, R$_2$, R$_5$, R$_6$ and R$_7$ are as defined above;
piperazines, for instance piperazines of formula E5:

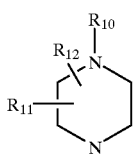
(E5)

where R$_{10}$ is as defined above and R$_{11}$ and R$_{12}$ independently represent an alkyl group, aryl group or COR$_9$ group;
piperidines, for instance piperidines of formula E6:

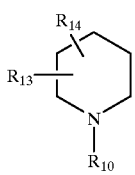
(E6)

where R$_{10}$ is as defined above and R$_{13}$ and R$_{14}$ each independently represent R$_{11}$, OH or an alkoxy group;

pyrrolidines, for instance pyrrolidines of formula E7:

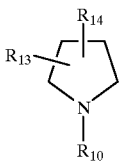
(E7)

where R$_{10}$, R$_{13}$ and R$_{14}$ are as defined above;
morpholines, for instance morpholines of formula E8:

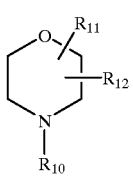
(E8)

where R$_{10}$, R$_{11}$ and R$_{12}$ are as defined above;
diamines, for instance diamines of formula E9:

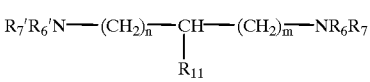
(E9)

where m and n each independently is 0–5 and where R$_{11}$ is as defined above and R$_6$' and R$_7$' independently thereof represent the same groups as R$_6$ and R$_7$;
ephedrines, for instance ephedrines of formula E10:

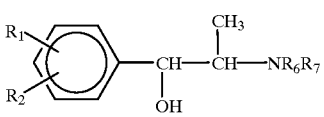
(E10)

where R$_1$, R$_2$, R$_6$ and R$_7$ are as defined above.
amino alcohols or amino ethers, for instance of formula E11a, E11b or E11c:

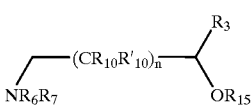
(E11a)

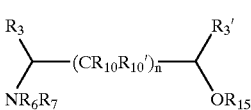
(E11b)

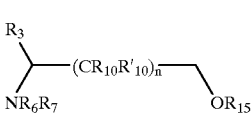
(E11c)

where n is 0–10, R$_{15}$=H or alkyl and where R$_{10}$' independently thereof represents the same groups as R$_{10}$ and R$_6$, R$_7$, R$_{10}$, R$_3$ and R$_3$' are as defined above;

1-(2-naphthyl)alkylamines, for instance 1-(2-naphthyl)alkylamines of formula E12:

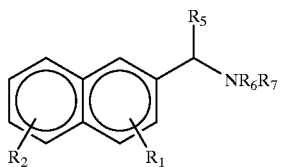
(E12)

where $R_1$, $R_2$, $R_5$, $R_6$ en $R_7$ are as defined above;
aliphatic amines, for instance aliphatic amines of formula E13:

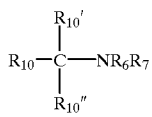
(E13)

where $R_6$, $R_7$, and $R_{10}$ are as defined above, and $R_{10}'$ and $R_{10}''$ are chosen from the same group as $R_{10}$ and are not the same as each other and as $R_{10}$;
phosphoric acids, for instance phosphoric acids of formula (E14):

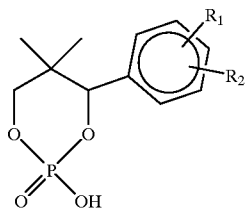
(E14)

where $R_1$ are $R_2$ as defined above;
carboxylic acids, for instance carboxylic acids of formula E15:

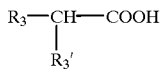
(E15)

where $R_3$ en $R_3'$ are as defined above;
substituted butane dicarboxylic acids for instance of formula (E16):

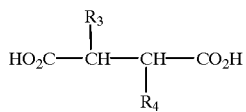
(E16)

where $R_3$ en $R_4$ are as defined above;
aromatic or aliphatic hydroxycarboxylic acids or derivatives thereof, in particular substituted mandelic acids, for instance α-hydroxycarboxylic acids of formula E17:

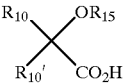
(E17)

where $R_{10}$, $R_{10}'$ and $R_{15}$, are as defined above and $R_{10}$ and $R_{10}'$ are different;
sulphonic acids, in particular (substituted) camphorsulphonic acids or (substituted) 1-phenylalkane-sulphonic acids of formula E18:

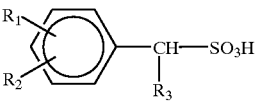
(E18)

where $R_1$, $R_2$ and $R_3$ are as defined above;
2-aryloxyalkanoic acids, in particular 2-aryloxypropionic acids of formula E19:

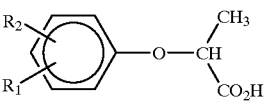
(E19)

where $R_1$ and $R_2$ are as defined above;
biaryl biacids, in particular biaryl bicarboxylic acids of formula E20:

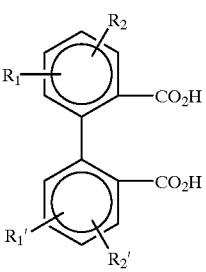
(E20)

where $R_1$ and $R_2$ are as defined above and $R_1'$ and $R_2'$ are independently thereof chosen from the same groups as $R_1$ and $R_2$;
substituted bi(hetero)aryldifosfinic oxides, particularly binaphthalene difosfinic oxides of formula E21:

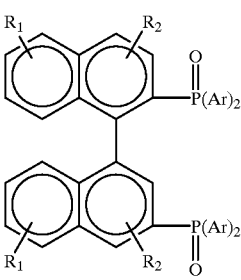
(E21)

wherein $R_1$ and $R_2$ are as defined above and are situated arbitrarily on the naphthalene skeleton, and Ar represents a (hetero)aryl group. The substituents $R_1$ with i=1–15 and Ar preferably contain 1–30, in particular 1–20 C-atoms and may or may not be substituted with an alkyl group, alkoxy group, carboxyl group, alkoxycarbonyl group, amino group, nitro group, thio group, thioalkyl group, nitrile group, hydroxy group, acyl group or halogen.

As is known to one skilled in the art, during crystallization inclusion of one or more solvent molecules may also take place. The diastereomer complex according to the invention may therefore also contain one or more molecules of a solvent. The ratio of the resolving agents to each other may vary within a wide range, with, in the case of salt formation, the sum of the acid groups and the sum of the basic groups in the complex having to be equal. It has, surprisingly, been found that after one or two recrystallizations the diastereomers according to the invention remain constant as regards the ratio of the resolving agents in the diastereomer upon further recrystallizations. This proves that the widespread ratio of resolving agents that is found is not the result of simple inclusion, for instance due to too rapid crystallization.

The invention also relates to an agent for separating a mixture of enantiomers, the agent comprising at least two resolving agents of which at least one is optically active. Preferably, the agent contains at least two resolving agents of the same type.

The invention also relates to a process for separating a mixture of enantiomers. This process is characterized in that the mixture of enantiomers is contacted in a suitable solvent with at least two resolving agents, at least one of which is optically active, yielding the diastereomer complex as described above. The sequence in which this takes place is not critical. In the process use is made of standard procedures and conditions that are generally known for separation of enantiomers via the formation of diastereomers. One skilled in the art can simply find out which principles and methods used for optimization of classical resolution processes can also be applied to the process according to the subject invention. One option is, for instance, to replace a portion of the resolution acids or bases with mineral acids or bases in order to optimize the use of the expensive resolving agents. Also, the result of the resolution may be strongly dependent on the molar ratio of resolving agent to the racemate. Such ratio may for instance be varied between 0,5 and 2.

Although this is not preferred, it is also possible to resolve a mixture of enantiomers by first adding one or more resolving agent(s) and, when no crystallization of a diastereomer takes place, add one or more further resolving agent(s), etc. This can be done by, for instance, adding 2–21, preferably 2–13 and in particular 2–7 resolving agents. It will be clear to one skilled in the art that this process is more time-consuming, for which reason the resolving agents are preferably added simultaneously, certainly at lab scale.

On an industrial scale the addition of the resolving agents will be chosen so that the crystallization is controllable and, for instance, no crystallization takes place at undesirable places in the installation and also the heat development per unit of time remains controllable. To achieve this, dosing in time of the combination of resolving agents can be adapted. Optionally, the resolving agents are added one after the other. The optimum way of adding the resolving agents can simply be determined by one skilled in the art.

The optically active resolving agents according to the invention preferably have an e.e. larger than 95%, in particularly larger than 98%, more in particular larger than 99%.

It has, surprisingly, also been found that when several optically active resolving agents are applied, these need not necessarily have the same absolute configuration. It has, for instance, been found that when use is made of three resolving agents A, B and C, a separation was possible both when A and B had, for instance, the S-configuration and C the R-configuration, and when A, B and C all had the S-configuration. The complex formed in both cases contained A and B as well as C, C in both cases having a different configuration. This may be useful in the cases where only one enantiomer of the relevant resolving agent is well obtainable.

Preferably, substantially only the diastereomer complex according to the invention crystallizes out with the highest possible e.e. of the separate compounds, following which it can be isolated using customary techniques. This may also involve chemical purification of the diastereomer complex. The process according to the invention can therefore also be applied to effect chemical purification of the mixture of enantiomers.

The conversion of the above-mentioned diastereomer complex to the enantiomers present in it is carried out in ways that are generally known to one skilled in the art, for instance by acid or base treatment followed by extraction, distillation or chromatography.

From practice it is known that the use of a mixture of two or more different solvents in crystallizations may sometimes give better results. If a mixture of solvents is used, this mixture for instance consists of 2–5 different solvents, and in particular of 2–3. The process according to the subject invention can therefore also be carried out using a mixture of two or more different solvents.

The invention will be elucidated on the basis of examples.
Definitions and syntheses
P-mix
Phencyphos, P1, (1,3,2-dioxaphosphorinane,-5,5-dimethyl-4-phenyl-2-hydroxy-2-oxide)
Chlocyphos, P2, (1,3,2-dioxaphosphorinane,-5,5-dimethyl-4-(2'-chlorophenyl)-2-hydroxy-2-oxide)
Anicyphos, P3, (1,3,2-dioxaphosphorinane,-5,5-dimethyl-4-(2'-methoxyphenyl)-2-hydroxy-2-oxide) were prepared and resolved according to Ten Hoeve and Wijnberg, U.S. Pat. No. 4,814,477.
W-mix
W1, Dibenzoyltartaric acid,
W2, Di-p-toluoyltartaric acid were obtained from Aldrich.
W3, Di-p-anisoyltartaric acid was prepared and resolved following literature procedures.
A-mix
A1, Mandelic acid was obtained from Aldrich,
A2, p-methylmandelic acid
A3, p-fluoromandelic acid were prepared and resolved following literature procedures.
Other mandelic acid analogs, p-methoxymandelic acid, p-bromomandelic acid and p-chloromandelic acid were prepared and resolved following literature procedures.
PEA I-mix
p-Br-PEA, p-Br-phenethylamine was prepared according to: J.A.C.S. 105, 1578–84 (1983) via Leuckhart synthesis from commercially available p-Br-acetophenone (Aldrich). Resolution see Example I.3; Table 1. p-Cl-PEA, p-Cl-phenethylamine was prepared as above from p-Cl-acetophenone (Aldrich). Resolution see Example I.6 and I.7; Table 1. p-$CH_3$-PEA, p-$CH_3$-phenethylamine was prepared as above A from p-$CH_3$-acetophenone (Aldrich). Resolution see Example I.4 and I.5; Table 1. Resolution of rac. PEA I-mix see E; Examples IX—XI.

PEA II-mix

PEA, phenethylamine (Aldrich), p-NO$_2$-PEA, p-NO$_2$-phenethylamine and o-NO$_2$-PEA, o-NO$_2$-phenethylamine p-NO$_2$-PEA and o-NO$_2$-PEA were prepared as a 1:1 mixture as described in the literature from optically pure PEA (Aldrich). The mixture is applied with a ratio PEA : p-NO$_2$-PEA : o-NO$_2$-PEA =1:1:1

PEA IIA-mix,

D-NO$_2$-PEA and o-NO2-PEA as 1:1 mixture.

PEA IIB-mix

PEA and p-NO$_2$-PEA as 1:1 mixture

Pure p-NO$_2$-PEA was obtained via crystallization of the HCl salt.

PEA III-mix m-MeO-PEA, m-CH$_3$O-phenethylamine m-Cl-PEA, m-Cl-phenethylamine m-Br-PEA, m-Br-phenethylamine were synthesized following the same procedure used for the synthesis of the para analogues. Resolution or rac. PEA III-mix see E; Example XII Other PEA analogs (from the o-, m-, and p-series) were synthesized following the known procedure.

BA I-mix

α-Me-BA, α-methylbenzylamine (Aldrich);

α-Et-BA, α-ethylbenzylamine and

α-iP-BA, α-isopropylbenzylamine were synthesized following literature procedures. Resolution of BA I-mix see E; Example XIII A. Small scale resolution of amines with the P-mix, W-mix and A-mix

EXAMPLE I

General procedure

To a solution of the racemic (rac.) amine (1–10 mmol) to be resolved in a solvent as indicated in table 1 was added one molequivalent of the P-, W- or A-mixture, each as a 1:1:1 mixture of its components.

The resulting mixture was heated to reflux (in some cases a clear solution was not obtained) and the mixture was allowed to cool to room temperature (RT). The solid was collected by suction, dried and analyzed by $^1$H-NMR (200 MHz, DMSO(dimethylsulphoxide)-d6).

The enantiomeric excess (e.e.) of the amines was determined by chiral HPLC after isolating the free amine from the salt by treatment with 10% NaOH solution and extraction with organic solvent. Columns used are listed below together with their indication number in Table 1.

Chiral HPLC columns:

1: Crownpak Cr
2: Chiralpak AD
3: Chiralcel OD
4: Chiralcel OB
5: Chiralcel oJ
6: R,R Whelk
7: Ultron ES OVM The salt was recrystallized from the indicated solvent(s) and again analyzed; the number of recrystallizations is indicated in table I together with the solvent. On small scale the yields were not determined. The results of the small scale resolutions are summarized in Table 1, wherein the indication of the solvent by A, B, C . . . stands for:

A: 2-butanone
B: ethanol (EtOH)
C: 2-propanol
D: methanol (MeOH)
E: ethylacetate (EtOAc)
F: toluene
G: water The ratio mix P1/P2/P3 refers to the molar ratio of compound P1:P2:P3 present in the solid.

TABLE 1

| entry ref. | amine | mix (–) | solvent | no. of recryst. (solvent) | ee (%) | HPLC | ratio mix P1/P2/P3 etc. |
|---|---|---|---|---|---|---|---|
| 1 | p-MeO-phenethylamine | P | A/B | 1 | 65 | 1 | 7:9:0 |
| 2 | | W | A/B | 1 | 56 | 1 | 0:1:2 |
| 3 | p-Br-phenethylamine | A | A | 1 | 96 | 1 | 1:5:0 |
| 4 | p-Me-phenethylamine | W | B | 1 (G) | 50 | 1 | 1:1:1 |
| 5 | | A | C | 1 | 96 | 1 | 1:5:0 |
| 6 | p-Cl-phenethylamine | P | C | 1 (B) | 92 | 1 | 3:3:4 |
| 7 | | A | C | 1 (D) | 94 | 1 | 1:5:0 |
| 8 | o-Cl-phenethylamine | P | A | 1 (A/B) | 99** | 1 | 20:0:1 |
| 9 | | W | B | 2 | 95 | 1 | 1:5:20 |
| 10 | | A* | A | 1 | 75 | 1 | 1:1 |
| 11 | o-Br-phenethylamine | A* | A/C | 1 (C) | 90 | 1 | 1:1 |
| 12 | o-Me-phenethylamine | P | A | 0 (D) | 51 | 2**** | 1:0:0 |
| 13 | | W | A/C | 1 (D) | 10 | 2**** | 1:3:2 |
| 14 | | A* | A/C | 1 | 90 | 2**** | 1:1 |
| 15 | m-MeO-phenethylamine | P | A/C | 1 (D) | 80 | 1 | 5:4:1 |
| 16 | | A* | A/C | 1 | 94 | 1 | 1:10 |
| 17 | m-Me-phenethylamine | P | A/C | 1 (C) | 99** | 1 | 5:5:1 |
| 18 | | A | F | 1 | 99 | 1 | 2:5:2 |
| 19 | m-Cl-phenethylamine | A* | A/C | 1 (C) | 99 | 1 | 1:4 |
| 20 | m-Br-phenethylamine | P | A/C | 1 (D) | 50 | 1 | 3:3:1 |
| 21 | m-Br-phenethylamine | A* | A/C | 1 (C) | 99 | 1 | 1:4 |
| 22 | cis-2-phenylhydroxy-piperidine | W | C | 1 | 99 | 2 | 5:1:1 |
| 23 | α-methylphenylalanine | P | B | 1 | 92 | 1 | 4:1:2 |
| 24 | α-methylphenylalanine amide | P | A | 1 | 99 | 1 | 2:1:3 |
| 25 | | W | A | 1 | 33 | 1 | 1:8:6 |
| 26 | 5-ethyl-5-methyl-2-fenyl-4-imidazolidinone (cis & trans) | P | A | 1 (A/D) | 98 | 1 | 4:1:0 |

TABLE 1-continued

| entry ref. | amine | mix (–) | solvent | no. of recryst. (solvent) | ee (%) | HPLC | ratio mix P1/P2/P3 etc. |
|---|---|---|---|---|---|---|---|
| 27 | 3-quinuclidinol | P | A/D | 1 | ca. 66*** | 2 | 1:1:2 |
| 28 | 3-quinuclidinol-benzoic ester | W | D | 1 (D/G) | 98** | 2 | 1:10:4 |
| 29 | N-methyl-2-allyl-2-(3,4-dichlorophenyl)-ethylamine | P | A | 1 | 75 | 2 | 5:1:3 |
| 30 | N-ethyl-2-aminoethyl-pyrrolidine | P | A | 1 (A/C) | 89*** | 2 | 4:1:0 |
| 31 | α-ethynylbenzylamine | P | C | 2 | 95 | 2 | 6:1:1 |
| 32 |  | W | A/C | 1 | 90 | 4 | 2:1:4 |
| 33 | trans-N-benzyl-3,4-diphenylpyrrolidine | W | C | i | 97 | 2 | 6:1:1 |
| 34 | trans-3,4-diphenyl-pyrrolidine | W | A | 1 (A/D) | 99 | 2**** | 1:3:3 |
| 35 |  | P | A/D | 1 (A/D) | 95 | 2**** | 2:1:1 |
| 36 | p-hydroxyphenyl-glycine | P | B/G | 1 | 95 | 1 | 1:2:3 |
| 37 | p-fluorophenylglycine nitrile | P | A | 1 | 98 | 2 | 20:2:1 |
| 38 |  | W | A | 1 | 35 | 2 | n.d. |
| 39 | p-fluorophenylglycine methylester | P | A | 1 (B) | 94 | 1 | 15:3:2 |
| 40 | 3-ethylmorfoline | W | B | 2 | 96** | 2**** | 0:2:1 |
| 41 | 2-aminobutanol | A* | A | 1 | >98 | 2**** | 2:3 |
| 42 | α-isopropylbenzylamine | P | A | 1 (C) | 80 | 1 | 20:1:1 |
| 43 | α-ethylbenzylamine | P | A | 1 (C) | 72 | 1 | 1:1:1 |

*mix of only A1 and A2
**repeated on preparative scale
***HPLC analysis via benzoate
****HPLC analysis via tosylate Examples of Preparative Resolutions

EXAMPLE II

The experiment of example I.8 was repeated on a larger scale.

To a solution of rac. o-Cl-PEA (57.5 g; 366 mmol) in 800 ml EtOH was added a mixture of (–)-phencyphos (84 g) and (–)-anicyphos (4 g). The mixture was heated at reflux (no clear solution) and cooled to RT. The solid was collected and recrystallized from 1.5 l EtOH. Yield 42 g (HPLC 90% e.e.). This salt was recrystallized from 650 ml EtOH to afford 22.1 g (15%) salt with >99% e.e.

EXAMPLE III

The experiment of example I.17 was repeated on a larger scale.

20.5 g (150 mmole) racemic 3-methyl-phenylethylamine was dissolved in 900 ml 2-propanol and 13.35 g (50 mmole) (–)-chlocyphos, 13.6 g (50 mmole) (–)-anicyphos and 12.1 g (50 mmole) (–)-phencyphos were added. Heated to reflux and after addition of 50 ml MeOH a clear solution was obtained. The heating was stopped and the solution was stirred for 18 hours. The salt was collected, rinsed with 2-propanol and wet salt (HPLC 78% e.e.) recrystallized from 500 ml 2-propanol and 120 ml MeOH, yielding 11.6 g (18%) salt with 96% e.e. (HPLC).

EXAMPLE IV

The experiment of example I.28 was repeated on a larger scale.

To a solution of 3-quinuclidinol-benzoate (30 g, 126 mmol) in MeOH (1,2 l) was added a mixture of Di-p-anisoyl-L-tartaric acid (17 g, 34 mmol), Di-p-toluoyl-L-tartaric acid (30.6 g, 76 mmol) and Dibenzoyl-L-tartaric acid (4.4 g, 11 mmol). The mixture was heated to reflux and cooled to RT. The resulting salt was heated at reflux in MeOH/water (8:2) (1 l) for 10 min. and cooled to RT. The salt was collected and treated with 10% NH$_4$OH/TBME. The quinuclidinolbenzoate (12 g, 40%) was enantiomerically pure (>98%) by HPLC.

The benzoate was converted to enantiomerically pure (+)-(S)-quinuclidinol by treatment with 10% HCl (reflux, 16 hours).

EXAMPLE V

The experiment of Example I.40 was repeated on a larger scale.

4.55 g (30 mmole) racemic 2-ethylmorpholine was dissolved in 100 ml EtOH (96%) and a solution of 3.76 g (10 mmole)(–)-dibenzoyltartaric acid, 4.0 g (10 mmole)(–)-ditoluoyltartaric acid and 4.36 g (10 mmole) (–)-dianisoyltartaric acid in 100 ml EtOH (96%) was added at once. Crystallization started within 30 minutes and stirring was continued for another hour. The salt was collected, rinsed with EtOH (HPLC 70% e.e.) and recrystallized from 100 ml EtOH before complete drying. This yielded 2.6 g (30%) salt with 88% e.e. Another recrystallization from EtOH yielded 1.6 g (19%) salt with 96% e.e.

EXAMPLE VI

Resolution of DL-3-amino-3-phenylpropionic acid with P-mix

A mixture of racemic 3-amino-3-phenylpropionic acid (990 mg, 6 mmol) and (–)P-mix (2 mmol each) in 15 ml 2-butanone was heated to reflux. The clear solution was allowed to cool to room temperature. After stirring for 1 hour at room temperature the solid was collected by suction, washed with 1 ml 2-butanone and dried, yielding 804 mg salt. The solid was analyzed by $^1$H-NMR, showing a mixture of phencyphos, chlocyphos and anicyphos in a molar ratio of 5:4:1.

An enantiomeric excess of >98% was determined by chiral HPLC (Crownpack CR (+)).

C. Small scale resolution of acids with the PEA-mixes

EXAMPLE VII

General Procedure

To a solution of the racemic acid (1–10 mmol) in the solvent as indicated(see list) was added one molequivalent of the PEA mixture each as a 1:1(:1) mixture of its components. Solvents:
A: 2-butanone
B: ethanol (EtOH)
C: 2-propanol
D: methanol (MeOH)
E: ethylacetate (EtOAc)
F: toluene
G: water The resulting mixture was heated to reflux (in some cases a clear solution was not obtained) and the mixture was allowed to cool to room temperature (RT). The solid was collected by suction, dried and analyzed by $^1$H-NMR (200 MHZ, DMSO-d6).

The enantiomeric excess (e.e.) of the amines was determined by chiral HPLC after isolating the free acid from the salt by treatment with 10% HCl solution and extraction with organic solvent. Columns used are listed below:

Chiral HPLC Columns:
1: Crownpak Cr
2: Chiralpak AD
3: Chiralcel OD
4: Chiralcel OB
5: Chiralcel OJ
6: R,R Whelk
7: Ultron ES OVM The salt was recrystallized from the solvent(s) as indicated and again analyzed. On small scale the yields were not determined. The results of the small scale resolutions are summarized in Table 2.

The ratio mix refers to the molar ratio of the compounds of the mix present in the solid, in the sequence as given in the definition of the mixes.

TABLE 2

| entry ref. | acid | mix (+) | solvent | no. recryst. (solvent) | ee | HPLC | ratio mix |
|---|---|---|---|---|---|---|---|
| 1 | p-Me mandelic acid | PEA IIA | A | 1 (B/D) | 96 | 2 | 4:1 |
| 2 | | PEA IIB | A/D | 1 | 99 | 2 | 1:4 |
| 3 | p-fluoro-mandelic acid | PEA IIA | A | 1 (A/D) | 98 | 2 | 10:1 |
| 4 | | PEA IIB | A | 0 | 99 | 2 | n.d. |
| 5 | p-Br-mandelic acid | PEA II | A | 1 (A/D) | 99 | 2 | 15:1:0 |
| 6 | | PEA I | A | 1 | 99 | 2 | n.d. |
| 7 | p-Cl-mandelic acid | PEA II | A | 1 (A/D) | >95 | 2 | 35:1:0 |
| 8 | | PEA I | A | 1 | 93 | 2 | n.d. |
| 9 | m-Me-mandelic acid | PEA I | A/C | 0 | 67 | 2 | n.d. |
| 10 | 2-(p-Cl-phenoxy)propionic acid | PEA I | E | 1 (E) | 88 | 2 | n.d. |
| 11 | 3-chloro-iso-butyric acid | PEA I | C | 1 | 59 | 2 | n.d. |
| 12 | 2-phenylbutyric acid | PEA I | A | 1 (A/C) | 85 | 2 | n.d. |
| 13 | | PEA II | A | 1 | 90 | 2 | 4:1:0 |
| 14 | 2-(p-Br-phenyl)butyric acid | PEA I | A | 1 | 75 | 2 | n.d. |
| 15 | | PEA II | A | 1 (C) | 95 | 2 | 1:0:0 |
| 16 | phenylsuccinic acid | PEA I | A | 1 (A/D) | 90 | 3 | n.d. |
| 17 | benzylsuccinic acid | PEA II | A | 1 (C) | 88 | 3 | 2:2:1 |
| 18 | | PEA* III | A | 1 (C) | 57 | 3 | n.d. |

*((−)-mix)

D. Resolution with a N-acyl-fenylglycine-mix

EXAMPLE VIII

Resolution of cis-1-aminoindan-2-ol with N-acyl-phenylglycine mix 992 mg cis-1-aminoindan-2-ol and a mix of N-benzoyl-D-phenylglycine, N-toluoyl-D-phenylglycine and N-p- anisoyl-D-phenylglycine (2 mmol each) in 20 ml toluene and 5 ml butanone was heated to reflux and allowed to cool to room temperature. The solid was isolated, washed with 1 ml of toluene and dried. In this way 380 mg salt was obtained.

HPLC analysis showed N-benzoyl phenylglycine, N-toluoyl phenylglycine and N-anisoyl phenylglycine with a molar ratio of 1:1.6:0.9.

The e.e. of (−)-cis-1-aminoindan-2-ol was 82% (chiral HPLC, Crownpack CR (−)).

Recrystallization of the salt from 5 ml toluene and 2 ml 2-butanone gave 180 mg salt with N-benzoyl phenylglycine, N-toluoyl phenylglycine and N-anisoyl phenylglycine in a molar ratio of 1:1.8:0.8. The e.e. of the (−)-cis-1-aminoindan-2-ol was 96%.

E. Resolution of mixtures of racemic (rac) mixtures of enantiomers

EXAMPLE IX

Resolution of rac. PEA-I-mix with (R)-p-CH$_3$-mandelic acid ((R)-p-Me-MA)

To a mixture of rac. p-Br-PEA, p-Cl-PEA and p-Me-PEA (100 mmol each) in 600 ml EtOH (96%) was added (R)-p-Me-MA (300 mmol, 50 g). The mixture was refluxed and allowed to cool to room temperature (RT). The solid was collected and recrystallized from EtOH (500 ml). The solid was collected and dried. Yield 33 g (35%). The mixed salt contained of (R)-p-Br-PEA, (R)-p-Cl-PEA and (R)-p-Me-PEA in 1:1:1 ratio. The salt was treated with 10% NaOH/TBME and the PEA I-mix was isolated as a slightly yellow oil. HPLC analysis (1) showed all three amines with e.e. >98%.

EXAMPLE X

Resolution of rac. PEA I-mix with (S)-p-Me-mandelic acid and (S)-p-Br-mandelic acid To a mixture of rac. p-Br-PEA, p-Cl-PEA and p-Me-PEA (13 mmol each) in 200 ml EtOH (96%) was added a mixture of (S)-p-Br-MA and (S)-p-Me-MA (20 mmol each)). The mixture was refluxed and allowed to cool to RT. The solid was collected and recrystallized from EtOH (100 ml). The solid was collected and dried. Yield 6 g (43%). The mixed salt contained (S)-p-Br-PEA, (S)-p-Cl-PEA and (S)-p-Me-PEA in 1:1:1 ratio and of (S)-p-Br-MA and (S)-p-Me-MA (1:1). The salt was treated with 10% NaOH/TBME and the PEA I-mix was isolated as a slightly yellow oil. HPLC analysis (1) showed all three amines with e.e. >98%.

EXAMPLE XI

Resolution of rac. p-MeO-PEA in the presence of rac. PEA-I-mix with (R)-p-CH$_3$-mandelic acid To a mixture of rac. p-MeO-PEA, p-Br-PEA, p-Cl-PEA and p-Me-PEA (10 mmol each) in 60 ml EtOH (96%) was added (R)-p-Me-MA (40 mmol 6,5 g). The mixture was refluxed and allowed to cool to RT. The solid was collected and recrystallized from EtOH (50 ml). The solid was collected and dried. HPLC analysis (1) showed that the mixed salt consisted of all four amines with a ratio of 3:52:30:13 respectively. The e.e. of all four amines were >98%.

Note: p-MeO-PEA could not be resolved with the A-Mix but could be resolved in the presence of other PEA amines.

EXAMPLE XII

Resolution of rac. PEA III-mix

To a mixture of m-MeO-PEA, m-Cl-PEA, and m-Br-PEA (100 mmol each) in EtOH (600 ml) was added (S)-p-Me MA (45 g, 300 mmol). The mixture was heated to reflux and allowed to cool to RT overnight. The solid was collected and dried, yield 34 g (38%). The salt was treated with 10 NaOH/TBME and 16,8 g of the PEA III mix was isolated. HPLC analysis (1) showed a 2:4:4 ratio with an e.e. >98%.

EXAMPLE XIII

Resolution of rac. BA I-mix 50 g (0.33 mole) rac. α-isopropylbenzylamine, 45 g (0.33 mole) rac. α-ethylbenzylamine and 24.2 g (0.2 mole) S-(−)-α-methylbenzylamine were dissolved in 1.5 l IPA and 208 g (0.86 mole) (+)-Phencyphos was added. The mixture was heated to reflux and 1.0 l EtOH was added to get a clear solution. The mixture was allowed to cool to room temperature under stirring for 18 hours, the salt was collected.

A sample of the mixture of resolved amines was liberated from the salt and HPLC showed 90% e.e. for the two resolved amines. The salt was recrystallized from 1.2 l EtOH, yielding 60 g (26%) salt with >98% e.e. for all 3 amines. The ratio of the amines was 4:6:1 (α-methyl; α-ethyl; α-isopropyl) as determined by GC (120° C.).

An experiment without S-(−)-α-methylbenzylamine added, yielded a salt with both other amines with 40% e.e. and a recrystallization gave an e.e. of 70%.

Separate resolution experiments with a-isopropylbenzylamine and α-ethylbenzylamine with (+)-phencyphos gave e.e.'s below 5%.

EXAMPLE XIV

Resolution of rac. anicyphos, chlocyphos and 2,4-dichlocyphos with (−)-ephedrine To a mixture of rac. anicyphos, chlocyphos and 2,4-dichlocyphos (1,3,2-dioxaphosphorinane-5,5-dimethyl-4(2', 4'-dichlorophenyl)-2-hydroxy-2-oxide) (10 mmol each) in 2-propanol (250 ml) was added (−)-ephedrine (30 mmol). The mixture was heated to reflux and allowed to cool to RT. The solid was collected and recrystallized from 2-propanol. The mixed salt was treated with 10% HCl for 30 min. and the solid collected. HPLC analysis (6) showed (+)-anicyphos, (+)-chlocyphos and (+)-2,4-dichlocyphos in a ratio of 55:35:5 with e.e.'s >98%.

EXAMPLE XV

Resolution of rac. anicyphos, chlocyphis and 2,4-dichlocyphos with (−)-p-hydroxyphenylglycine To a mixture of rac. anicyphos, chlocyphos and 2,4-dichlocyphos (10 mmol each) in EtOH/water (8:2) was added (−)-p-hydroxyphenylglycine (30 mmol). The mixture was heated to reflux and allowed to cool to RT. The solid was collected and treated with 10% HCl for 30 min. The acids were collected by suction. HPLC analysis (6) showed anicyphos, chlocyphos and 2,4-dichlocyphos in a ratio of 1:35:65 with e.e.'s 98%.

F. Resolution of a racemate with a mixture of resolving agents of which some are racemic and others enantiomerically pure.

EXAMPLE XVI

Resolution of rac. p-Br-PEA with p-Br-mandelic acid and p-Me-MA a) Using (S)-p-Br-mandelic acid and (S)-p-Me-MA.

To a mixture of rac. p-Br-PEA (2 g) in MeOH was added a mixture of (S)-p-Br-mandelic acid and (S)-p-Me-MA (1 g each). The salt was collected and analysed by $^1$H-NMR (MA 1:1) and HPLC (1). The e.e. of the amine was 84%.

b) Using rac-p-Br-mandelic acid and (S)-p-Me-MA.

To a mixture of rac. p-Br-PEA (2 g) in MeOH was added a mixture of rac. p-Br-MA and (S)-p-Me-MA (1 g each). The salt was collected and analysed by $^1$H-NMR (MA 3:4) and HPLC (1) and (2). The e.e. of the amine was 90% and the e.e. of p-Br-MA 95%.

c) Using (S)-p-Br-mandelic acid and rac. p-Me-MA

To a mixture of rac. p-Br-PEA (2 g) in MeOH was added a mixture of (S)-p-Br-mandelic acid and rac. p-Me-MA (1 g each). The salt was collected and analysed by $^1$H-NMR (MA 4:3) and HPLC (1) and (2). The e.e. of the amine was 99% and the e.e. of p-Me-MA >95%.

EXAMPLE XVII

Resolution of p-Cl-PEA with the P-mix containing racemic phencyphos

To a solution of rac. p-Cl-PEA in 2-butanone was added a mixture of (−)-anicyphos, (−)-chlocyphos and rac. phencyphos (1 g each). The resulting salt was recrystallized from EtOH and analysed by HPLC (1) and (6). The amine had an e.e. of 84% and the phencyphos an e.e. of 80–85%.

EXAMPLE XVIII

Resolution of chlocyphos with (−)-ephedrine and (+)-phencyphos

To a solution of (−)-ephedrine (2,4 g) in 2-propanol (50 ml) was added (+)-phencyphos (1,75 g) and rac. chlocyphos (1,85 g). The mixture was heated to reflux and allowed to cool to RT. The salt (3,31 g) was treated with 10% KOH/toluene. The organic layer was acidified and the solid analysed with HPLC (6). Both (+)-phencyphos and (+)-chlocyphos were enantiomerically pure (>98%).

EXAMPLE XXI

Resolution of phencyphos with (+)-ephedrine and (−)-chlocyphos

To a solution of (+)-ephedrine (2,6 g) in 2-propanol (70 ml) was added rac.-phencyphos (1,90 g) and (−)-chlocyphos (2,04 g). The mixture was heated to reflux and allowed to cool to RT. The salt (2,78 g) was treated with 10% KOH/toluene. The organic layer was acidified and the solid analysed with HPLC (6). Both (−)-phencyphos and (−)-chlocyphos were enantiomerically pure (>98%).

Note: Phencyphos could not be resolved with ephedrine but could be resolved with ephedrine in the presence of chlocyphos.

EXAMPLE XX

Resolution of rac. N-benzyl-3,4-bis-(p-methoxyphenyl)-pyrrolidine with (−)-N-benzyl-3,4-diphenylpyrrolidine and (−)-di-(p-anisoyl)-tartaric acid To a mixture of rac. N-benzyl-3,4-bis-(p-methoxyphenyl)-pyrrolidine (1,2 g) and (−)-N-benzyl-3,4-diphenylpyrrolidine (1 g) in 2-butanone (50 ml) was added (−)-di-(p-anisoyl)-tartaric acid (2,4 g). The mixture was heated to reflux and cooled to RT. The resulting salt was recrystallized twice from 2-butanone. HPLC analysis (2) showed N-benzyl-3,4-bis-(p-methoxyphenyl)-pyrrolidine and (−)-N-benzyl-3,4-diphenylpyrrolidine in a 1:10 ratio with an e.e. of 93% for N-benzyl-3,4-bis-(p-methoxyphenyl)-pyrrolidine.

Note: we have not been able to resolve this amine via resolution with a single resolving agent, nor using the P-mix or the W-mix in the absence of N-benzyl-3,4-diphenylpyrrolidine.

G. Resolution of (a) racemic amine(s) with a mixture of enantiomerically pure mandelic acids and a non chiral acid (phenylacetic acid)

EXAMPLE XXI 1.35 (10 mmole) racemic p-CH$_3$-phenethylamine was dissolved in 25 ml IPA and 500 mg (3.3 mole) R-(−)-mandelic acid, 550 mg (3.3 mmole) R-(−)-p-CH$_3$-mandelic acid and 450 mg (3.3 mmole) phenylacetic were added. Under reflux a clear solution was obtained which was allowed to cool to room temperature and the salt was collected after 1 hour. $^1$H NMR of the salt showed all 3 acids present and HPLC of the free amine showed 82% e.e.

The same experiment with p-Cl-phenethylamine yielded a salt which also included all 3 acids (68% e.e.)

An experiment with 1.35 g (10 mmole) racemic p-CH$_3$-phenethylamine, 830 mg (5 mmole) R-(−)-p-CH$_3$-mandelic acid and 680 mg (5 mmole) phenylacetic acid in 25 ml IPA yielded a salt containing both acids and amine with 90% e.e.

An experiment with 1.35 g (10 mmole) racemic p-CH$_3$-phenethylamine and 1.66 g (10 mmole) R-(−)-p-CH$_3$-mandelic acid in 50 ml IPA yielded a salt with 57% e.e.

H. Resolution of rac. amines with mixtures containing resolving agents with opposite configuration

EXAMPLE XXII

Resolution of the PEA I-mix (ratio: 1:1:1) with substituted mandelic acids with opposite configuration The results are summarized in Table 3.

TABLE 3

| exp. nr. | resolv. | Eq | solvent | yield salt | e.e. mix amines |
|---|---|---|---|---|---|
| 1 | (S)-p-CH$_3$-MA | ½ | MeOH | 28% | 94% |
|   | (R)-MA | ½ |   |   |   |
| 2 | (S)-p-CH$_3$MA | ½ | MeOH | 10% | 80% |
|   | (S)-MA | ½ |   |   |   |

Exp. 1: yield after recr. 12% e.e. after recr. 99% salt: p-CH$_3$-MA:MA=9:1

Exp. 2 salt: p-CH$_3$-MA:MA=4:1

EXAMPLE XXIII

Resolution of p-Me-PEA with substituted mandelic acids with opposite configuration The results are summarized in table 4.

TABLE 4

| exp. nr. | resolv. | Eq | solvent | yield salt | e.e. mix amines |
|---|---|---|---|---|---|
| 1 | (S)-p-CH$_3$-MA | ½ | MeOH | 14% | 87% |
|   | (S)-MA | ½ |   |   |   |
| 2 | (S)-p-CH$_3$-MA | ½ | EtOH | 14% | 90% |
|   | (R)-MA | ½ |   |   |   |
| 3 | (S)-p-CH$_3$-MA | ½ | MeOH | 10% | 83% |
|   | (rac)-MA | ½ |   |   |   |

Exp. 1: salt p-CH$_3$-MA:MA=4:1

Exp. 2: salt p-CH$_3$-MA:MA=6:1

EXAMPLE XXIV

Resolutions of o-Cl PEA with phosphoric acids with opposite configuration

The results are summarized in Table 5.

TABLE 5

| exp. nr. | resolv. | Eq | solvent | e.e. amine | P$_1$; P$_2$ |
|---|---|---|---|---|---|
| 1 | (−)-P$_1$ | ½ | EtOH | 67% | 6:1 |
|   | (−)-P$_2$ | ½ |   |   |   |
| 2 | (−)-P$_1$ | ½ | EtOH | 70% | 8:1 |
|   | (+)-P$_2$ | ½ |   |   |   |
| 3 | (−)-P$_1$ | ½ | EtOH | 66% | 6:1 |
|   | rac-P$_2$ | ½ |   |   |   |

I. Resolution (via inclusion) of 1-phenylethanol using mixtures of TADDOL derivatives

EXAMPLE XXV (4R,5R)-2,2-dimethyl-α,α,α',α'-tetraphenyl-1,3-dioxolan-4,5-dimethanol (TADDOL I), (4R,5R)-2,2-dimethyl-α,α,α',α'-tetra(p-methoxyphenyl)-1,3-dioxolan-4,5-dimethanol (TADDOL II) and (4R,5R)-2,2-dimethyl-α,α,α',α'-tetra(p-methylphenyl)-1,3-dioxolan-4,5-dimethanol (TADDOL III) were prepared according to literature.

To a mixture of TADDOL 1 (1.0 g) and TADDOL II (1.1 g) in 20 ml benzene was added racemic 1-phenylethanol (PE) and the mixture was evaporated. To the residue 50 ml hexane was added and the suspension was stirred overnight. The precipitate was collected and $^1$H NMR showed all 3 components present in a 2:2:1 ratio (TADDOL I: TADDOL II:PE). The enriched alcohol was isolated by distillation of the precipitate (0.1 mmHg: 80° C.). HPLC (Chiralcel OD) showed 82% e.e.

J. Comparative resolutions of α-methylhenylalanine amide using P- and W-mix and separate components

EXAMPLE XXVI

Resolutions were on a 1 mmole scale in 2-butanone, using the general procedure. Results are summarized in table 6.

TABLE 6

| Resolving agent | e.e. (%) |
|---|---|
| P-mix | 98 |
| P1 | 55 |
| P2 | 57 |
| P3 | 33 |
| W-mix | 33 |
| W1 | — |
| W2 | 16 |
| W3 | 13 | for HPLC see Example I.25.

K. The attainment of a constant composition on repetitive crystallization

EXAMPLE XXVII

To a solution of (−)-ephedrine (3.6 g) in 75 ml i-propanol was added a (+)-P-mix (5.1 g). The mixture was heated to reflux and cooled to RT. After one recrystallization from i-propanol a mixed salt was obtained with a constant composition (ephedrine/phencyphos/chlocyphos; 2:2:1), which did not change on repeated recrystallization from i-propanol.

To a solution of 1.8 g (20 mmole) rac. 2-amino-1-butanol in a mixture of 5 ml IPA and 30 ml 2-butanone was added 3.2 g (20 mmole) (−)-A mix and after heating to reflux a clear solution was obtained, which was allowed to cool to room temperature with stirring and after 3 hours the mixed salt was collected. After one recrystallization from 2-butanone the mixed salt had the same composition. (alcohol: M.A.:p-Me-M.A.=5:2:3).

L. Fast screening of resolving agents

An equimolar mixture of 11 resolving acids (11-acid-mix) containing of: (−)-P1, (−)-P2, (−)-P3, (−)-W1, (−)-W2, (−)-W3, (−)-A1, (−)-A2, (−)-malic acid, (−)-phenylsuccinic acid and (+)-camphorsulphonic acid was used in Examples XXVIII and XXIX.

EXAMPLE XXVIII 2.9 g (11 mmole) 11-acid-mix was dissolved in 80 ml IPA (isopropylamine) under reflux and 1.72 g (11 mmole) rac. 2-chloro-a-phenetylamine was added to the hot solution. The mixture was allowed to cool to room temperature under stirring and the salt was collected after 18 hours. The salt composition was determined by $^1$H NMR. The main components were the amine and the W1, W2 and W3 acids. The e.e. of the amine was 40% (HPLC). Recrystallization from IPA/MeOH (2:1) did not change salt composition but e.e. increased to 84% (HPLC).

EXAMPLE XXIX 2.9 g (11 mmole) 11-acid-mix was dissolved in 50 ml IPA under reflux and 1.5 g (11 mmole) rac. α-ethylbenzylamine was added. Crystallization started within 1 minute and the mixture was allowed to cool to room temperature under stirring. The salt was collected after 2 hours and $^1$H NMR showed that the salt consisted of the amine and acids W1, W2 and W3. The e.e. of the amine was 10% by HPLC. The salt was recrystallized from 50 ml IPA+100 ml MeOH and the composition did not change ($^1$H NMR) but e.e. of the amine increased to 22%.

Examples XXX–XXXII show fast screenings of resolving agents according to the invention which result in a single resolving agent.

EXAMPLE XXX

Resolution of racemic α-methyl-benzylamine with N-acetyl-L-amino acid-mix a) To a solution of 1.25 g (10 mmol) of racemic a-methyl-benzylamine in 10 ml of toluene, 3 ml of isopropanol and 1 drop of water, was added a mixture of 6N-acetyl-L-amino acids (1.6 mmol each).

The mix was prepared from the following L-amino acids: L-Phe, L-Tyr, L-Try, L-phenylglycine, L(+)-p-hydroxyphenylglycine and S-indoline-2-carboxylic acid. The mixture was heated to reflux and the clear solution cooled to room temperature. After stirring for 2 hours at room temperature the resulting solid was isolated, washed with 1 ml of toluene and dried, yielding 131 mg salt.

HPLC analysis showed salt formation with only N-acetyl-L-p-hydroxyphenylglycine. Chiral HPCL (Crownpack CR(−)) gave e.e.=62%.

b) Subsequently a mixture of 720 mg (6 mmol) racemic α-methylbenzylamine and 1.26 g N-acetyl-L-p-hydroxyphenylglycine (6 mmol) in 20 ml toluene, 20 ml isopropanol and 3 ml water was heated to reflux and the clear solution cooled to room temperature. After stirring for 1 hour at room temperature the solid was isolated, washed with 2 ml of toluene and dried. 637 mg (32%) salt was obtained with e.e.=94% (chiral HPLC, Crownpack CR (−)).

EXAMPLE XXXI

Resolution of cis-1-aminoindan-2-ol with N-acetyl-L-amino acid mix a) 990 mg racemic cis-1-aminoindan-2-ol and the same N-acetyl-L-amino acid-mix was used in Example XXX (1.6 mmol each) in 12 ml 2-butanone and 3 ml Isopropanol was heated to reflux and cooled to room temperature.

After stirring for 4 hours the resulting solid was isolated, washed with 1 ml of 2-butanone and dried, yielding 180 mg salt.

HPLC analysis of the salt showed the presence of only N-acetyl-S-indolinecarboxylic acid and an e.e. of 36% (Crownpack CR (−)).

b. Subsequently 500 mg racemic cis-1-aminoindan-2-ol and 648 mg N-acetyl-S-indolinecarboxylic acid in 30 ml 2-butanone and 5 drops of water were heated to reflux and the clear solution cooled to room temperature.

After stirring for 4 hours at roomtemperature the solid was isolated, washed with 1 ml of 2-butanone and dried. 326 mg salt was obtained (yield 29%).

The (−)-cis-1-aminoindan-2-ol had e.e.=98% (chiral HPLC, Crownpack CR (−)).

EXAMPLE XXXII

Resolution of dl-mandelic acid with L-amino-acid-amide-mix 910 mg (6 mmol) di-mandelic acid, 160 mg NaOH-50% and a mix of L-tyrosine amide, L-phenylalanine amide. HCl and L-phenylglycine amide (2 mmol each) in 10 ml ethanol 96% was heated to reflux.

The clear solution was allowed to cool to room temperature.

After stirring for 1.5 hours the solid was isolated, washed with 2 ml of ethanol 96% and dried. The yield was 310 mg.

HPLC and $^1$H NMR analysis showed a salt with only L-phenylglycine amide.

The mandelic acid was isolated via treatment with hydrochloric acid and extraction with toluene. After evaporation, the residue was solved in 6 ml of water and the concentration of mandelic acid measured with HPLC.

The optical rotation of this solution was measured: $[\alpha]_D$=−146 (25° C., c=0.47). From this value an e.e. of 95% was calculated.

This provides us with a fast screening method for resolving agents which in general will look like this:

Add a mix of resolving agents (for instance acids or amines) to the racemate and determine the composition of the salt and the e.e. of the resolved enantiomer. If the e.e., even after recrystallisation from a suitable solvent, is good enough then look which resolving agent(s) is/are responsible for the resolution and use this/these in subsequent resolution experiment. If the e.e. is not acceptable, even after recrystallisation from a suitable solvent, than start a new experiment without the resolving agents present in the first salt. By repeating this sequence as a rule one will end up with an acceptable e.e. and a salt composition reflecting the resolving agent which can be used in further resolutions, and can serve as a starting point for further optimalisation.

What is claimed is:

1. A diastereomer complex comprising at least three compounds of which at least two compounds are resolving agents in optically active form and at least one compound is an enantiomer in optically active form.

2. A diastereomer complex comprising at least three compounds of which at least one compound is a resolving agent in optically active form and at least two compounds which are enantiomers in optically active form.

3. A diastereomer complex according to claim 1, wherein said complex is a salt.

4. A diastereomer complex according to claim 2, wherein said complex is a salt.

5. A diastereomer complex according to claim 1 or 3, contains at least three resolving agents in optically active form.

6. A diastereomer complex according to claim 1 or 3, which contains at least three enantiomers in optically active form.

7. A diastereomer complex according to any one of claims 1 or 3 wherein the enantiomer in optically active form is a carboxylic acid, an amine, an alcohol, an amino acid, an amino alcohol, or a thiol.

8. A diastereomer complex according to any one of claims 1 or 3 wherein at least one enantiomer is present in an enantiomeric excess larger than 95%.

9. A diastereomer complex according to any one of claims 1 or 3 wherein said at least one compound is a mixture of enantiomers which are selected from the group consisting of those represented by formulae E1 through E21:

(E1)

wherein:

$R_4$ represents an aryl group or an alkyl group, $R_6$ and $R_7$ represent independently of each other, H or alkyl $R_9$ represents OH, alkoxy, or $NH_2$, $R_{10}$ represents H, alkyl or aryl, and, $R_4$ is not the same as $R_{10}$;

(E2)

wherein $R_4$, $R_6$, $R_7$ and $R_{10}$ are as defined above:

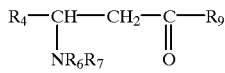
(E3)

wherein and $R_4$, $R_6$, $R_7$ and $R_9$ are as defined above:

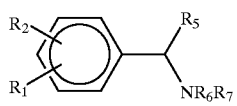
(E4)

wherein $R_1$ and $R_2$, each independently represent H, an alkyl group, or an aryl group, $R_5$, represents an alkyl group; and $R_6$ and $R_7$ are as defined above;

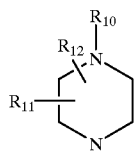
(E5)

wherein $R_{10}$ is as defined above and $R_{11}$ and $R_{12}$ independently represent an alkyl group, an aryl group or a $COR_9$ group; and $R_9$ is as defined above;

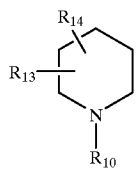
(E6)

wherein $R_{10}$ is as defined above and $R_{13}$ and $R_{14}$ each independently represent $R_{11}$ as defined above, OH or an alkoxy group;

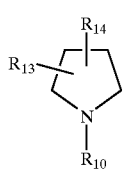
(E7)

wherein $R_{10}$, $R_{13}$ and $R_{14}$ are as defined above;

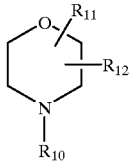
(E8)

wherein $R_{10}$, $R_{11}$ and $R_{12}$ are as defined above;

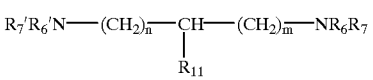
(E9)

wherein m and n each independently is 0–5, $R_{11}$ is as defined above, $R_6$ and $R_7$ are as defined above, and $R_6'$ and $R_7'$ independently thereof represent the same groups as $R_6$ and $R_7$;

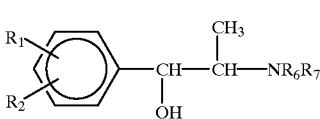
(E10)

wherein $R_1$, $R_2$, $R_6$ and $R_7$ are as defined above;

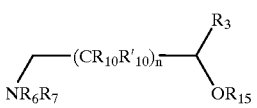
(E11a)

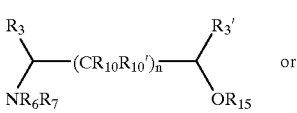
(E11b)

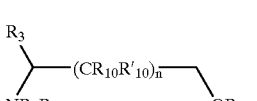
(E11c)

wherein n is 0–10, $R_{15}$ is H or alkyl, $R_{10}'$ independently thereof represents the same groups as $R_{10}$, $R_6$, $R_7$ and, $R_{10}$, are as defined above, and $R_3$ and $R_3'$ independently represent an alkyl group or an aryl group;

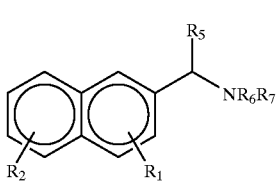
(E12)

wherein $R_1$, $R_2$, $R_5$, $R_6$ and $R_7$ are as defined above;

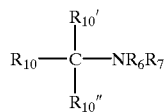
(E13)

wherein $R_6$, $R_7$, and $R_{10}$ are as defined above, and $R_{10}'$ and $R_{10}''$ are selected from the same group as $R_{10}$ and are not the same as each other and as $R_{10}$;

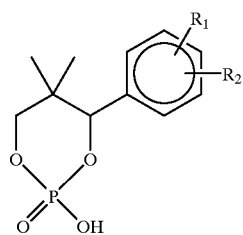
(E14)

wherein $R_1$ and $R_2$ as defined above;

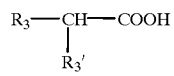
(E15)

wherein $R_3$ and $R_3'$ are as defined above;

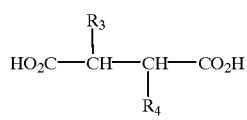
(E16)

wherein $R_3$ and $R_4$ are as defined above;

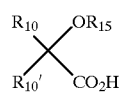
(E17)

wherein $R_{10}$, $R_{10}'$ and $R_{15}$ are as defined above and $R_{10}$ and $R_{10}'$ are different;

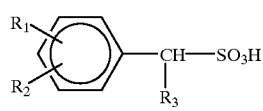
(E18)

wherein $R_1$, $R_2$ and $R_3$ are as defined above;

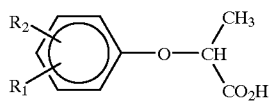
(E19)

wherein $R_1$ and $R_2$ are as defined above;

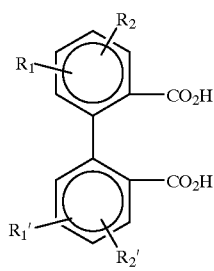
(E20)

wherein $R_1$ and $R_2$ are as defined above, and $R_1'$ and $R_2'$ are independently thereof selected from the same groups as $R_1$ and $R_2$;

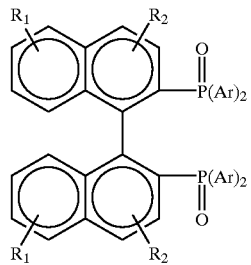
(E21)

wherein $R_1$ and $R_2$ are as defined above and are situated arbitrarily on the naphthalene skeleton, and Ar represents a (hetero)aryl group.

10. A diastereomer complex according to claim 1 or 3, wherein the resolving agents are selected from the group consisting of the resolving agents represented by formulae S1 and including formula, through S14:

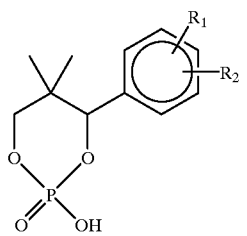
(S1)

wherein $R_1$ and $R_2$ each independently represent H, an alkyl group or an aryl group;

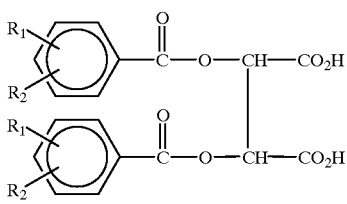

(S2)

wherein, and $R_2$ are as defined above;

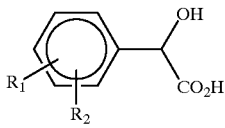

(S3)

wherein $R_1$ and $R_2$ are as defined above;

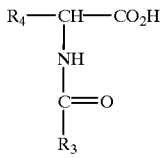

(S4)

wherein $R_3$ has a fixed meaning within a group, selected from the group consisting of an alkyl group and an aryl group, and $R_4$ represents an aryl group or an alkyl group, or wherein $R_4$ has a fixed meaning within a group, selected from an aryl group, or an alkyl group, and $R_3$ represents an alkyl group or an aryl group;

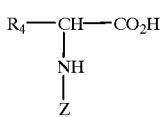

(S5)

wherein $R_4$ is as defined above;

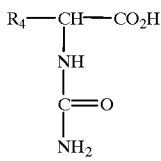

(S6)

wherein $R_4$ is as defined above;

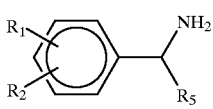

(S7)

wherein $R_1$ and $R_2$ may vary within a group as defined above and $R_5$ has a fixed meaning, and represents an alkyl group, or wherein $R_1$ and $R_2$ are fixed choices from the groups as defined above and $R_5$ varies within the alkyl group;

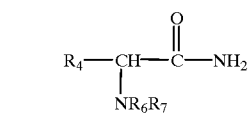

(S8)

wherein $R_4$ is as defined above, and $R_6$ and $R_7$ are selected independently of each other from H and alkyl;

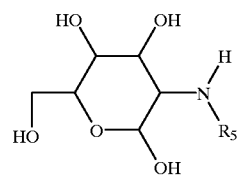

(S9)

wherein $R_5$ is as defined above;

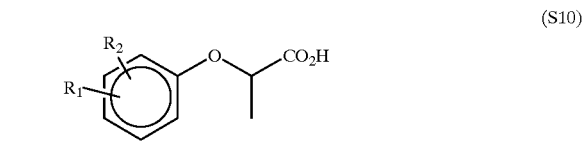

(S10)

wherein $R_1$ and $R_2$ are as defined above;

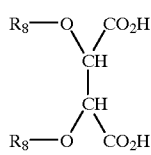

(S11)

wherein $R_8$ represents methyl or benzyl;

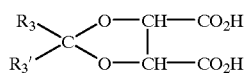

(S12)

wherein $R_3$ is as defined above and $R_3'$ is independently selected from the same groups but is not equal to $R_3$;

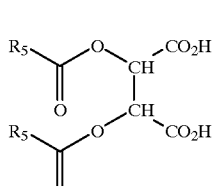

(S13)

wherein $R_5$ is as defined above;

(S14) 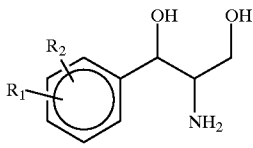

wherein $R_1$ and $R_2$ are as defined above.

11. A diastereomer complex according to claim 8, wherein the enantiomer in optically active form is a carboxylic acid, an amine, an alcohol, an amino acid, an amino alcohol, or a thiol.

12. A diastereomer complex according to claim 8, wherein said at least one compound is a mixture of enantiomers which are selected from the group consisting of those represented by formulae E1 through E21:

(E1) 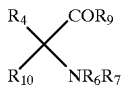

wherein:

$R_4$ represents an aryl group or an alkyl group $R_6$ and $R_7$ represent, independently of each other, H or alkyl, $R_9$ represents OH, alkoxy, $NH_2$, $R_{10}$ represents H, alkyl and aryl, and $R_4$ is not hte same as $R_{10}$;

(E2) 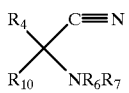

wherein $R_4$, $R_6$, $R_7$ and $R_{10}$ are as defined above;

(E3) 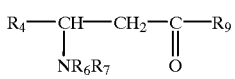

wherein $R_4$, $R_6$, $R_7$ and $R_{10}$ are as defined above;

(E4) 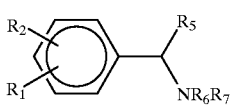

wherein $R_1$, and $R_2$ each independently represents H, an alkyl group, or an acyl group, $R_5$ represents an alkyl group, and $R_6$ and $R_7$ are as defined above;

(E5) 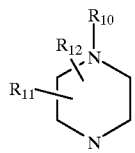

wherein $R_{10}$ is as defined above and $R_{11}$ and $R_{12}$ independently represent an alkyl group, an aryl group or a $COR_9$ group; and $R_9$ is as defined above;

(E6) 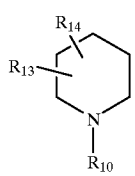

wherein $R_{10}$ is as defined above and $R_{13}$ and $R_{14}$ each independently represent $R_{11}$ as defined above OH or an alkoxy group;

(E7) 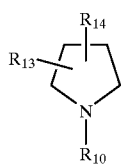

wherein $R_{10}$, $R_{13}$ and $R_{14}$ are as defined above;

(E8) 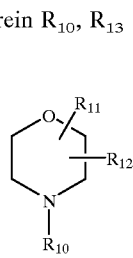

wherein $R_{10}$, $R_{11}$ and $R_{12}$ are as defined above;

(E9) 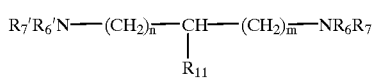

wherein m and n each independently is 0–5, $R_{11}$ is as defined above, $R_6$ and $R_7$ are as defined above, and $R_6'$ and $R_7'$ independently thereof represent the same groups as $R_6$ and $R_7$;

(E10) 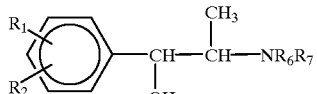

wherein $R_1$, $R_2$, $R_6$ and $R_7$ are as defined above;

(E11a)
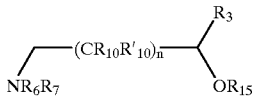

(E11b)
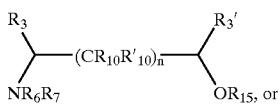

(E11c)
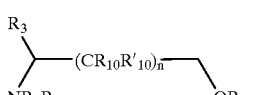

wherein n is 0–10, $R_{15}$ is H or alkyl, $R_{10}'$ independently thereof represents the same groups as $R_{10}$, $R_6$, $R_7$ and $R_{10}$ are as defined above, and $R_3$ and $R_3'$ independently represent an alkyl group or an aryl group (E12)
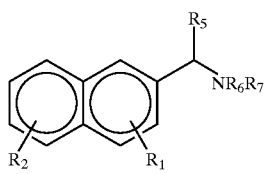

wherein $R_1$, $R_2$, $R_5$, $R_6$ and $R_7$ are as defined above;

(E13)
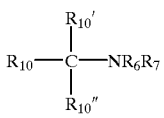

wherein $R_6$, $R_7$, and $R_{10}$ are as defined above, and $R_{10}'$ and $R_{10}''$ are selected from the same group as $R_{10}$ and are not the same as each other and as $R_{10}'$, (E14)
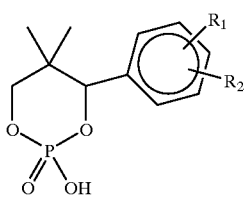

wherein $R_1$ and $R_2$ are as defined above;

(E15)
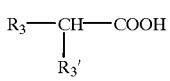

wherein $R_3$ and $R_3'$ are as defined above;

(E16)
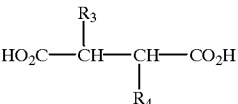

wherein $R_3$ and $R_4$ are as defined above;

(E17)
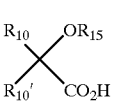

wherein $R_{10}$, $R_{10}'$ and $R_{15}$ are as defined above and $R_{10}$ and $R_{10}'$ are different;

(E18)
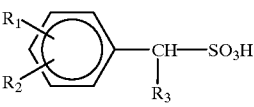

wherein $R_1$ $R_2$ and $R_3$ are as defined above;

(E19)
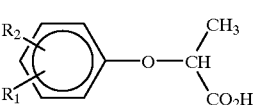

wherein $R_1$ and $R_2$ are as defined above;

(E20)
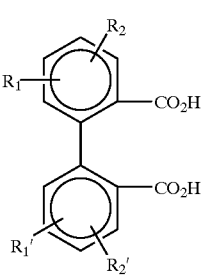

wherein $R_1$ and $R_2$ are as defined above, $R_1'$ and $R_2'$ are independently thereof selected from the same groups as $R_2$ and $R_2'$;

(E21)
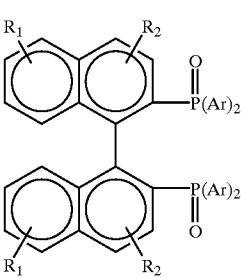

wherein $R_1$ and $R_2$ are as defined above and are situated arbitrarily on the naphthalene skeleton, and Ar represents a (hetero)aryl group.

13. A diastereomer complex according to claim 8, wherein the resolving agents are selected from consisting of the resolving agents represented by formulae $S_1$ through S14:

(S1)

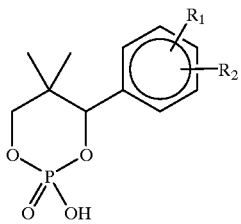

wherein $R_1$ and $R_2$ each independently represent H, an alkyl group or an aryl group;

(S2)

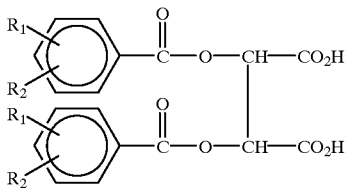

wherein$_1$ and $R_2$ are as defined above;

(S3)

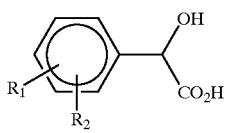

wherein $R_1$ and $R_2$ are as defined above;

(S4)

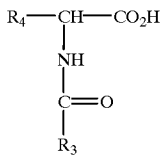

wherein $R_3$ has a fixed meaning within a group, selected from the group consisting of an alkyl group and an aryl group, and $R_4$ represents an aryl group or an alkyl group, or wherein $R_4$ has a fixed meaning within a group, selected from an aryl group, or an alkyl group, and $R_3$ represents an alkyl group or an aryl group;

(S5)

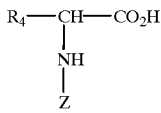

wherein $R_4$ is as defined above;

(S6)

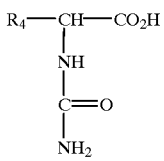

wherein $R_4$ is as defined above;

(S7)

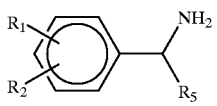

wherein $R_1$ and $R_2$ may vary within a group as defined above and $R_5$ has a fixed meaning, and represents an alkyl group, or wherein $R_1$ and $R_2$ are fixed choices from the groups as defined above and $R_5$ varies within the alkyl group;

(S8)

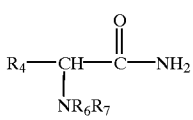

wherein $R_4$ is as defined above, and $R_6$ and $R_7$ are selected independently of each other from H and alkyl;

(S9)

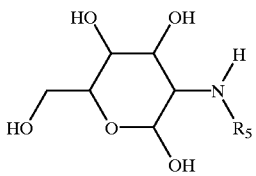

wherein $R_5$ is as defined above;

(S10)

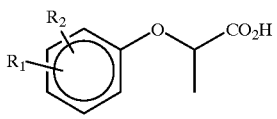

wherein $R_1$ and $R_2$ are as defined above;

(S11)

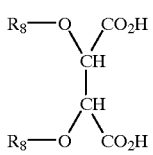

wherein $R_8$ represents methyl or benzyl;

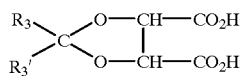
(S12)

wherein $R_3$ is as defined above and $R_3'$ is independently selected from the same groups but is not equal to $R_3$;

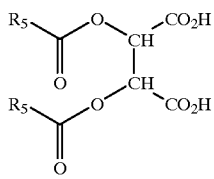
(S13)

wherein $R_5$ is as defined above;

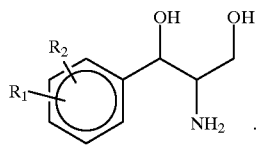
(S14)

14. A diastereomer complex according to claim 2, wherein said enantiomers are selected from the group consisting of α-amino acids, α-aminonitriles, β-amino acids, phenalkylamines, piperazines, piperidines, pyrrolidines, morpholines, diamines, ephedrines, amino alcohols, amino ethers, 1-(2-naphthyl) alkylamines, aliphatic amines, phosphoric acids, carboxylic acids, substituted butane carboxylic acids, aromatic hydroxycarboxylic acids, aliphatic hydrocarboxylic acids, sulphonic acids, 2-aryloxyalkanoic acids, biaryl acids, and substituted bi(hetero)aryldiphosphinic oxides.

15. A diastereomer complex according to claim 1, wherein the resolving agents are selected from the group consisting of substituted phosphoric acids, optically active tartaric acids, substituted α-hydroxycarboxylic acids, N-acylamino acids, N-benzyloxy carbonyl amino acids, N-carbamoyl amino acids, substituted phenalkylamines, amino acids amides, substituted N-glucosamines, aryloxypropionic acid, optically active ethers of tartaric acids, optically active acetals of tartaric acids, optically active alkanoylesters of tartaric acids, and phenylaminopropane diols.

* * * * *

UNITED STATES PATENT AND TRADEMARK OFFICE
CERTIFICATE OF CORRECTION

PATENT NO. : 6,235,927 B1
DATED : May 22, 2001
INVENTOR(S) : Vries et al.

It is certified that error appears in the above-identified patent and that said Letters Patent is hereby corrected as shown below:

<u>Title page,</u>
Please insert the correct ABSTRACT as follows:

ABSTRACT

A diastereomer complex obtained via a process for the separation of enantiomers is disclosed, wherein separation can be rapidly effected such that enantiomers are obtained with high e.e. values. The process permits the separation of mixtures of enantiomers in which more than one resolving agent is used, of which at least one resolving agent is optically active, and which yields a diastereomer complex containing at least two resolving agents in optically active form. The process provides for, inter alia, a diastereomer complex having at least three compounds of which at least two compounds are resolving agents in optically active form, and at least one compound is an enantiomer in optically active form. Also provided is a diastereomer complex having at least three compounds of which at least one compound is a resolving agent in optically active form, and at least two compounds which are enantiomers in optically active form.

Signed and Sealed this

Ninth Day of April, 2002

JAMES E. ROGAN
Director of the United States Patent and Trademark Office